United States Patent
Kaplowitz

(10) Patent No.: US 6,740,053 B2
(45) Date of Patent: May 25, 2004

(54) WATER JET FLOSSING APPARATUS

(75) Inventor: Gary H. Kaplowitz, University Place, WA (US)

(73) Assignee: Millenium Media Marketing, LLC, Tacoma, WA (US)

( * ) Notice: Subject to any disclaimer, the term of this patent is extended or adjusted under 35 U.S.C. 154(b) by 0 days.

(21) Appl. No.: 10/104,744

(22) Filed: Mar. 20, 2002

(65) Prior Publication Data

US 2003/0181837 A1 Sep. 25, 2003

(51) Int. Cl.[7] .......................... A61G 17/02; A61H 9/00
(52) U.S. Cl. .......................... 601/162; 601/165; 433/80
(58) Field of Search ........................ 601/154, 155, 601/159, 160, 161, 162, 163, 165, 169; 433/80, 89

(56) References Cited

U.S. PATENT DOCUMENTS

| | | | |
|---|---|---|---|
| 4,564,005 A | * 1/1986 | Marchand et al. | 601/165 |
| 4,854,869 A | 8/1989 | Lawhorn | 433/80 |
| 4,903,687 A | 2/1990 | Lih-Sheng | 128/66 |
| 5,027,798 A | 7/1991 | Primiano | 128/66 |
| 5,033,961 A | 7/1991 | Kandler et al. | 433/89 |
| 5,095,893 A | 3/1992 | Rawden | 128/66 |
| 5,220,914 A | 6/1993 | Thompson | 128/66 |
| 5,484,281 A | 1/1996 | Renow et al. | 433/80 |
| 5,667,483 A | * 9/1997 | Santos | 601/162 |
| 5,934,902 A | * 8/1999 | Abahusayn | 601/162 |
| 6,193,512 B1 | * 2/2001 | Wallace | 601/162 |
| 6,383,155 B1 | * 5/2002 | Hsia | 601/165 |

* cited by examiner

Primary Examiner—Nicholas D. Lucchesi
Assistant Examiner—Quang D. Thanh

(57) ABSTRACT

A water flossing apparatus for successful use with domestic water pressure service with its inherently higher flow rates. The apparatus contains a body 2 that is adapted to either shower, sink faucet or hose bibb connection, allowing for concurrent device and shower, device and sink or device and hose usage. The body contains a valve mechanism with lever 8 for regulating flow through the device and jet tip 14 whose bent end 15 is acutely angled beyond 90 degrees to the longitudinal axis of the hand piece to direct water out of the user's mouth. Directing water out of the user's mouth rather that towards the back of the user's throat, as occurs with the obtusely angled, slightly bend jet tips of the prior art, prevents the throat from being inundated with water and a gagging potential is thus mitigated.

11 Claims, 2 Drawing Sheets

WATER JET FLOSSING APPARATUS

FIELD OF INVENTION

This invention relates to fluid water jet oral cleansing devices, and most specifically to domestic water powered, water jet oral cleansing devices used with faucets, showers and hose bibbs.

BACKGROUND OF THE INVENTION

In the crowded, relatively recent art of water jet oral cleansing devices, a few inventions for use with sink or shower have been created, eliminating the need for electrical pump by using the available domestic water service pressure. Unique to domestic water driven devices is the relatively higher volume of water introduced into the user's mouth than that introduced by pump driven devices. This is evident because the inlet orifice size for either shower or faucet-mounted devices is greater. Further, the service pressure delivered, usually 30 to 120 psig, is considerably higher than that of the pump powered units, with their limited pump pressures exerted on small columns of water drawn from a static reservoir. The presence of a sink basin or shower tub that are capable by design to accommodate these high flow rates plus the added convenience of partaking of oral cleansing within the bathing regimen has made this a viable, albeit imperfect, alternative to countertop mounted, pump driven units. These higher volumes inherent with domestic water powered devices present a gagging potential to the users due to the head orientation when using a mirror, which is a common water-flossing accessory. A wall or shower mounted mirror provides the same visual feedback for water flossing that is afforded when brushing the teeth, string flossing at the sink or shaving within the shower. The generally head level height of the smaller, shower mounted mirrors requires the heads of the users to be either level or with the chin slightly raised when cleaning the upper teeth, and especially the back teeth. It is particularly in this scenario where the gagging potential is the greatest. Downward head tilting with mirror usage, as when water flossing the lower jaw, affords a measure of gravity drainage that helps to reduce this gagging potential. While shower or sink faucet valves do well in varying flow rates, there is a need to operate these faucet/shower devices at very low flow rates in order to prevent overly inundating the user's mouth with water during water flossing. While very low flow rates work well for sink connected devices, used solely for water flossing, they do not work well if concurrent faucet connected hose and device usage is desired. Further, low flow rates do not work well with shower units for the following reason. Of necessity, shower faucets must be set to higher flow rates due to the need for concurrent shower usage to prevent the bathing user from becoming chilled. It should be noted that without exception, the prior art for shower mounted devices anticipates the need for concurrent shower and flossing operation for this very reason. The need to reduce these volumes in shower connected devices while allowing for concurrent shower usage has led to the inclusion of separate volume controls included on most of the shower mounted water-flossing devices of the prior art. Michael J. Primiano, U.S. Pat. No. 5,027,798 shows a finger lever 58 that rotates circular member 52, whose projecting member 56 constricts the flow of water through tubing 16, thus adjusting flow. Alex and Barry Renow, U.S. Pat. No. 5,484,281 uses suppressor valve 44 to regulate the flow rate. Thomas W. Thompson, U.S. Pat. No. 5,220,914 presents a rotatable ball valve 24 that while being disclosed for the purpose of starting and stopping flow, could also be utilized to modulate flow rates. Although these aforementioned, prior art devices for shower use provide flow rate metering capability through these switches, suppressor valves, or levers, these domestic water powered devices still deliver much higher water volumes than their pump driven counterparts. These higher volumes contribute to a gagging potential, unique to these domestic water powered devices for other reasons elaborated below. It should be noted that in the instance where simultaneous sink and water-flossing would be performed, the same gagging potential exists, and the improvement of the present invention would be needed. The closest sink faucet mounted prior art device, Rawden, U.S. Pat. No. 5,095,893, provides for alternate sink or device usage by diverting flow with a pull stem 16 through either the device or into a sink basin. Clearly, Rawden does not disclose nor anticipate concurrent sink and device usage, as does the present invention. Another universal shortcoming in the shower mounted prior art that contributes to a gagging potential is that the ends of the various jet tips are only slightly to moderately bent, at an obtuse angle with respect to the longitudinal axis of the hand piece. A slightly bent tip's angularity directs the water predominantly towards the back of the user's throat. At best, the flow is directed downwards when these tips are bent at an approximate 90-degree angle with respect to the longitudinal axis of the hand piece with the user's arm in a horizontal orientation. It should be noted that whether directed towards the back of the user's throat or appreciably downward, inundation occurs in the aforementioned upper jaw cleaning, head tilting orientation while using a mirror. This problem is mitigated in the present invention whether applied to concurrent shower/device or faucet/device situations. In the specific application of providing concurrent hose and device usage, as would be desirable in a campground context, a different problem is encountered by reducing the flow for the device. If a hose is used, a higher flow rate than that desired for water flossing is produced. In the context of concurrent sink basin and device usage, the sink basin flow rates are slower than desired to fill the basin, drawing a glass of water or other uses. The art is in need of a water-flossing device that can be successfully used concurrently with a shower, garden hose or sink basin. The present single invention provides a working solution in either a concurrent shower, sink or hose use application.

Renow, U.S. Pat. No. 5,484,281, shows a hydro floss jet tip 46 being, used on a shower mounted device, bent less than 90 degrees, and another hydro floss 82 jet tip being bent at approximately 90 degrees to the longitudinal axis of the hand piece. Neither tip facilitates directing the flow out of the user's mouth as the present invention does.

Thompson, U.S. Pat. No. 5,220,914, shows a shower mounted plaque dislodge applicator 10 that is bent at approximately a 90 degree angle to the longitudinal axis of the hand piece and does not facilitate directing the flow out of the user's mouth as the present invention does.

Primiano, U.S. Pat. No. 5,027,798, while showing a variable pressure control capability on his shower mounted device, has a nozzle tip 38 that is bent less than 90 degrees to the longitudinal axis of the hand piece. Again, this does not facilitate directing the flow out of the user's mouth as the present invention does.

Rawden, U.S. Pat. No. 5,095,893, presents a faucet device that allows for alternate sink or device usage by means of a pull stem 16. It should be reiterated that Rawden provides a flow diverting capability for faucet use so that the cleaning device need not be disconnected between uses. Rawden, therefore, does not anticipate concurrent faucet and device usage as the present invention does. Further, while Rawden's device has provided a flow control knob 27 on the handle, his device has a bent tip that does not optimally redirect water out of the user's mouth. Rawden rightly indicates that the distal end 32 of tip 30 should be bent in his preferred embodiment. This tip, however, is shown bent at approximately 90 degrees to the longitudinal axis of the hand piece and does not facilitate directing the flow out of the user's mouth as the present invention does.

Lih-Sheng, U.S. Pat. No. 4,903,687, presents a portable, faucet attachable cleansing device with a water jet tip 5 that is appreciably parallel with the longitudinal axis of the hand piece thus directing water appreciably toward the back of the user's throat. It is noteworthy that this faucet-mounted device uses the faucet valve(s) exclusively to adjust flow volumes. Further, Lih-Sheng does not anticipate concurrent sink and device usage.

The less relevant prior art, used in context with dental practice applications is listed below. These dental devices are less relevant in that the context of their usage does not present the unique gagging problems associated with shower mounted devices as elaborated further below.

Kandler, U.S. Pat. No. 5,033,961, specifies that the distal end portion of cannula 17 is directed at an obtuse angle to the portion extending axially from socket 18. This angularity is appreciably less than 90 degrees to the longitudinal axis of the hand piece and does not facilitate directing the flow out of the user's mouth as the present invention does. It is evident that the context for this device is for use in a dental practice where a separate suction device is used concurrently, which eliminates inundation with its gagging potential.

Timothy M. Lawhorn, U.S. Pat. No. 4,854,869 in like manner provides a dental syringe whose angled tip of nozzle 7 is also only very slightly bent. As with Kandler, U.S. Pat. No. 5,033,961 above, it is also evident that the context for this device is for use in a dental practice where a separate suction device is used concurrently, thus preventing a gagging potential.

In summary, the prior art has not anticipated the unique higher flow rate problems encountered with domestic water powered oral irrigating devices wherein inundation at the back of the throat and gagging potential exist. Further, the art has not anticipated the concurrent use of hose and device usage, as disclosed in the present invention for the camping environment usage with a hose bibb connection or wash basin. As has been seen, the closest prior art device for faucet connection anticipates alternate sink and device usage by means of a pull stem 16 which diverts flow either through the device or into the sink (see Rawden, U.S. Pat. No. 5,095,893.) The art is still in need of a domestic water-flossing device whose jet tip is bent at an acute angle to direct the water appreciably out of the user's mouth in anticipation of the higher flow rates inherent with domestic water service pressures. The art is in need of a hose bibb, faucet mounted device that can effectively reduce flow rates through the device without reducing the hose flow rates detrimentally. Finally, the art is in need of a sink-mounted device that allows adequate flows for concurrent basin and device usage. The bent tip improvement of the present invention, although simple, is very effective in preventing water inundation at the back of the user's throat, with its associated gagging potential due to head orientation while using a mirror, which is a primary object of the present invention.

SUMMARY OF THE INVENTION

The present invention, in its preferred embodiment, is shower mounted water jet oral cleansing device affording the following advantages overcoming the shortcomings of the prior art;

a) A shower or faucet mounted water jet oral cleansing device whose jet tip end is bent beyond 90 degrees, at an acute angle to the longitudinal axis of the hand piece, thus directing accumulating water out of the user's mouth and greatly reducing the gagging potential due to higher flow rates inherent with domestic water pressures;

b) A shower or faucet mounted water jet oral cleansing device whose naturally higher flow rate associated with domestic water pressure operation and the desired faucet settings inherent with concurrent shower operation further serves to force accumulating water out of the user's mouth;

c) A shower or faucet mounted water jet oral cleansing device whose bent jet tip directs water away from the back of the throat of the user even when the head is tilted backwards for mirror observation of cleaning the upper jaw's back teeth, greatly reducing a gagging potential.

d) A faucet mounted water jet oral cleansing device whose domestic water connection allows for concurrent hose and device or sink and device usage without the need to absolutely divert flows into either sink/hose or device usage and without reducing hose or basin flow rates below optimal rates.

DETAILED DESCRIPTION OF PREFERRED EMBODIMENT

Figure 1:
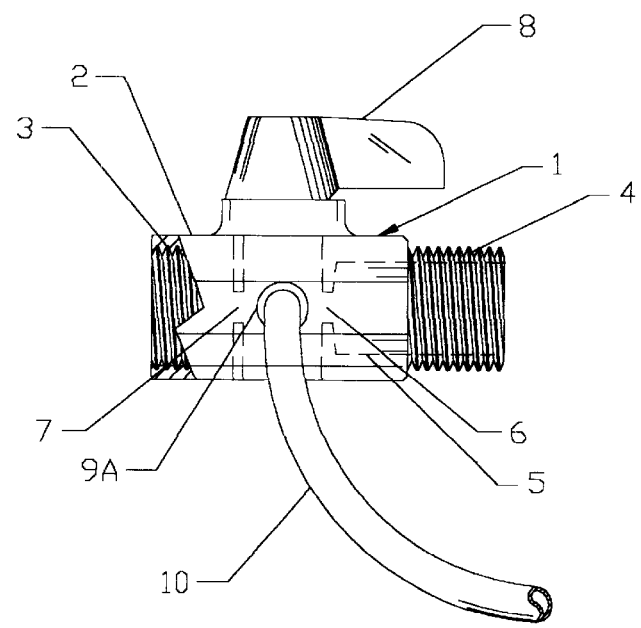
FIG. 1 shows the preferred embodiment of the Water jet flossing Apparatus as used in a shower.
Figure 1:
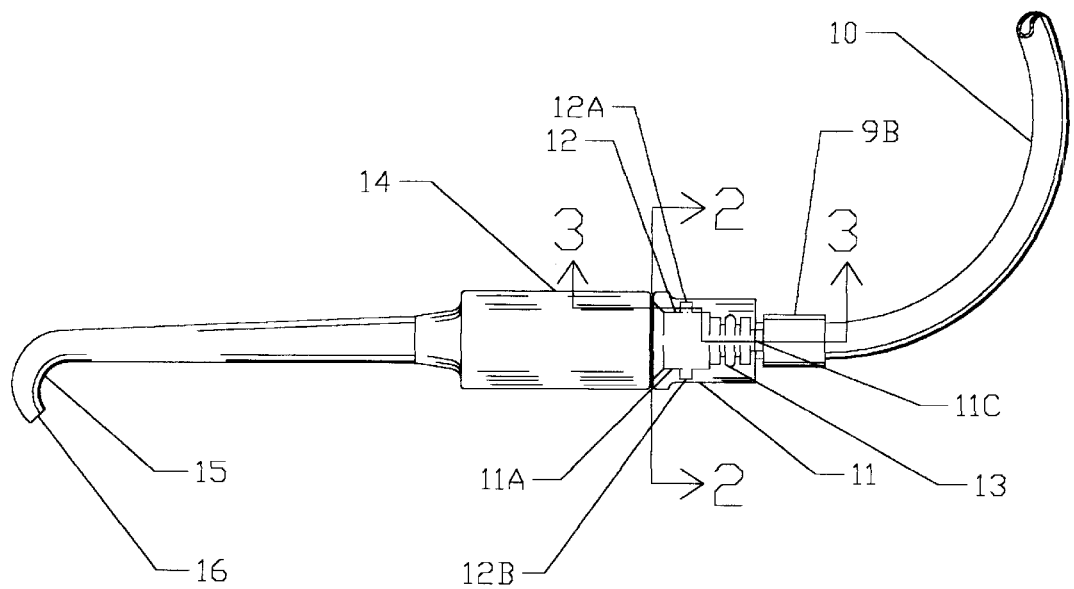
Figure 2:
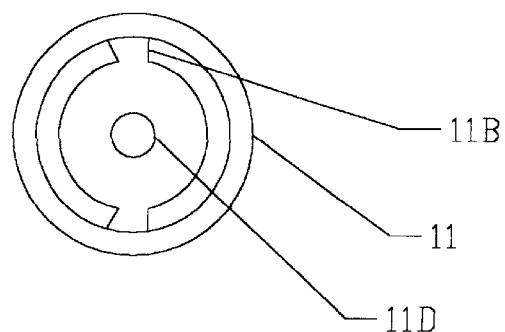
FIG. 2 shows an end view of adapter 11.
Figure 3:
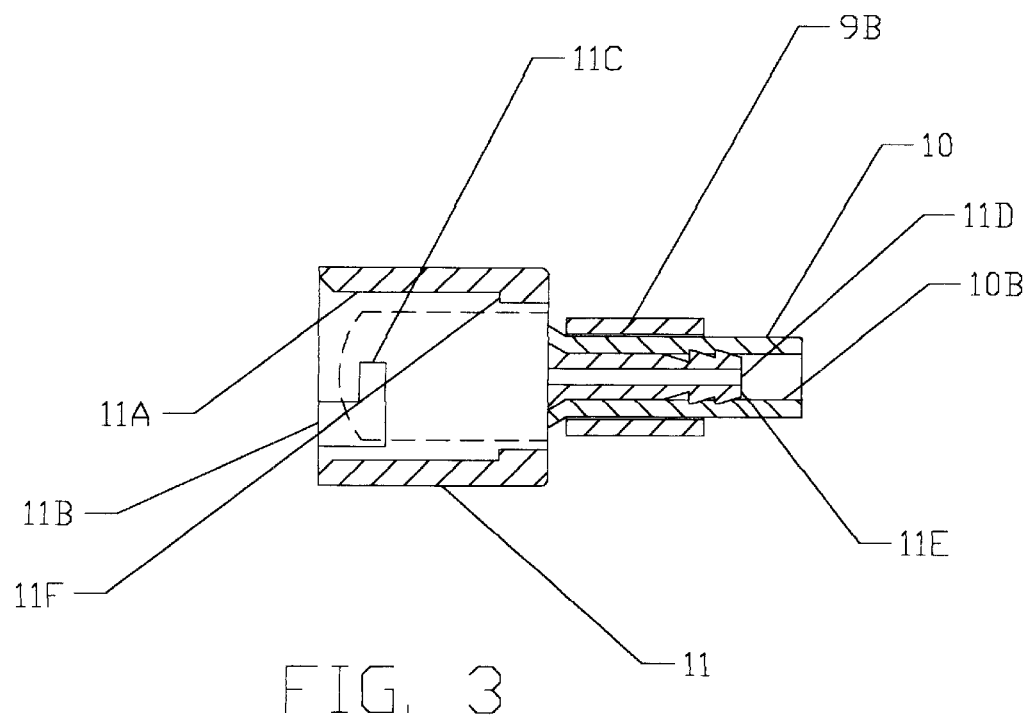
FIG. 3 shows an enlarged section taken through adapter 11.

Certain terminology is used herein for convenience only and is not to be taken as a limitation on the present invention. Referring to FIGS. 1, 2 and 3, FIG. 1 shows the Water jet flossing Apparatus 1. One end of shower connector valve body 2 has a female threaded orifice 3, providing a standard threaded plumbing connection to a showerhead stub. The opposite end of body 2 also has a male standard threaded connection 4 to accommodate a showerhead. Connection 4 contains a opening 5 for passage of water through the shower head for concurrent water flossing and shower usage. Orifice 6, sized for optimal velocity, regulates the flow of water through body 2. Orifice 7 is sized similarly for optimal velocity regulates and receives flow of water into body 2. Concurrently, a flow-regulating disk, well known to the art as commercially available from Vernay Laboratories Inc. of Yellow Springs, Ohio, part number VL3001-379, may be further employed to provide additional flow regulation for applications where very high domestic pressures are encountered. Valve lever 8 controls the flow rate through the device independent of the faucet setting and is connected to a standard ball valve mechanism that is well know in the art, is not shown for clarity and is not an object of the present invention. Inner Hose Surface 10A of Hose 10 (see FIG. 3) connects to body 2 using a standard laboratory type, tapered, ribbed nozzle connector, not shown, similar to that shown in FIG. 3, nozzle 11E. This nozzle creates interference fit with hose 10 to prevent leakage during use. Nylon bushing 9A slips over hose 10 further securing hose 10 to the standard hose nozzle and ultimately to body 2. Hose 10 is fabricated of a durable material capable of handling the full range of domestic water pressures encountered, which is generally 30 to 120 psig. The opposite end of hose 10 is similarly secured to adapter 11 using a standard laboratory, tapered, ribbed nozzle connector 11E (FIG. 3.) Nozzle 11E creates interference fit with Surface 10A. Orifice 11D allows flow through nozzle 11E. Nylon bushing 9B, in like manner, slips over hose 10, further securing the opposite end of hose 10 to adapter 11. Referring to FIG. 1 and FIG. 2, adapter 11 contains an orifice 11A that receives boss 12 of jet tip 14. Jet tip 14 is secured to adapter 11 by nib 12A and nib 12B entering slot 11B. Jet tip 14 is rotated inside of orifice 11A until the nib 12A and 12B of jet tip 14 contacts slot stop 11C. When so joined, "O" ring 13, located on boss 12, of jet tip 14, creates a tight seal between adapter 11 and boss 12 by firm contact of "O" ring 13 with step 11F. Referring to FIG. 1 and FIG. 3, jet tip 14 has a bent end 15, bent in excess of 90 degrees but not more than 150 degrees. In the preferred embodiment, bent end 15 of jet tip 14 is bent at 135 degrees from the longitudinal axis of the hand piece offering the best balance between downward and backward flow direction. It was found that at this angle provides the greatest ease for changing forward and downward components of flow force for the user requiring the least amount of either raising or lowering the elbow height during use while still directing the water out of the user's mouth. Bent tip 15 of jet tip 14 contains orifice 16, which can vary in diameter from 0.030" to 0.070". To lower the diameter range below 0.030" provided the minimal volumes, more akin to the pump driven units of the prior art at service pressures below 40 psig but proved to create a too high a pressure for comfortable use where domestic service pressures exceeded 70 psig. To exceed the larger diameter of 0.070" tended to provide excessive volumes when service pressures exceeded 80 psig albeit with adequate force when served by a domestic service pressures below 35 psig. The preferred embodiment's ideal orifice 16 diameter is 0.050" which affords the best balance between pressure and volumes through the full range of normal residential service pressures encountered of 30 to 120 psig.

It is to be understood that the form of the invention herein shown and described is to be taken as a preferred example of the same. Various changes in the shape, size, materials and arrangements of parts may be resorted to without departing from the spirit of the invention or the scope of the appended claims. Many other variations are possible. Consistent with the aforementioned concurrent sink and faucet usage scenario, the adaptation of this device for use when camping could include a standard garden hose connector in lieu of a faucet or shower head stub, threaded provision, for connecting the device to a campground hose bibb. The jet tip could be made of rigid, yet flexible rubber allowing for multidirectional flow within the user's mouth by physical contact with the teeth and gums. The device could further include separate flow restricting disks, as are well known in the art, to further regulate flows through the device where domestic service pressures are high, in addition to orifice 6 and orifice 7. Specifically, the 0.1 gallon/min. flow control disk which is commercially available from Vernay Laboratories Inc. of Yellow Spring, Ohio, part number VL3001-379 or others as are currently manufactured and available to the commercial market.

What is claimed is:

1. A domestic water pressure driven water-flossing apparatus comprised of;
    a) a valve body adapted to be connected to a threaded domestic water connection and device;
    b) said body having a lever regulating device flows and domestic water source and device usage;
    c) said body having an inlet orifice and an outlet orifice, sized to regulate flow rates through said body;
    d) said body having a tube nozzle receiving a hose;
    e) a concentric collar securing said hose to said nozzle;
    f) said hose having an opposite end;
    g) a jet tip adapter;
    h) said adapter having a second tube nozzle receiving said opposite hose end;
    i) a second concentric collar securing said opposite hose end to said second tube nozzle;
    j) a jet tip;
    k) said jet tip adapter having an orifice receiving a boss end of said jet tip;
    l) said boss end having an inlet orifice;
    m) said boss end having an "O"ring sealing connection of said boss end within said adapter orifice;
    n) said jet tip having a bent end whose bent angularity exceeds 90 degrees from the longitudinal axis of said jet tip;
    o) said jet tip having an outlet orifice.
2. The water-flossing apparatus of claim 1 wherein the jet tip is made of plastic.
3. The water-flossing apparatus of claim 1 wherein the jet tip is made of rubber.
4. The water-flossing apparatus of claim 1 wherein the hose is made of flexible plastic.
5. The water-flossing apparatus of claim 1 wherein the threaded domestic water connection is a sink faucet.

6. The water-flossing apparatus of claim 1 wherein the threaded domestic water connection is a showerhead stub.

7. The water-flossing apparatus of claim 1 wherein the threaded domestic water connection is a hose bibb faucet.

8. A shower mounted water-flossing apparatus comprised of;
   a) a valve body adapted to be connected to a shower head and device;
   b) said body having a standard, female threaded end connecting to a standard shower head stub and a standard, male threaded end connecting to a shower head;
   c) said body having a lever regulating device flows and concurrent shower and device usage;
   d) said body having an inlet orifice and an outlet orifice, sized to regulate flow rates through said body;
   e) said body having a tube nozzle receiving a hose;
   f) a concentric collar securing said hose to said nozzle;
   g) said hose having an opposite end;
   h) a jet tip adapter;
   i) said adapter having a second tube nozzle receiving said opposite hose end;
   j) a second concentric collar securing said opposite hose end to said second tube nozzle;
   k) a jet tip;
   l) said jet tip adapter having an orifice receiving a boss end of said jet tip;
   m) said boss end having an inlet orifice;
   n) said boss end having an "O" ring sealing connection of said boss end within said adapter orifice;
   o) said jet tip having a bent end whose bent angularity exceeds 90 degrees from the longitudinal axis of said jet tip;
   p) said jet tip having an outlet orifice.

9. The shower mounted water-flossing apparatus of claim 1 wherein the jet tip is made of plastic.

10. The shower mounted water-flossing apparatus of claim 1 wherein the jet tip is made of rubber.

11. The shower mounted water-flossing apparatus of claim 1 wherein the hose is made of flexible plastic.

* * * * *